United States Patent [19]

Bauman et al.

[11] 4,425,438

[45] Jan. 10, 1984

[54] ASSAY METHOD AND DEVICE

[76] Inventors: David S. Bauman, P.O. Box 1151, Norman, Okla. 73070; Paul A. Barstad, 1129 Robinhood La., Norman, Okla. 73701

[21] Appl. No.: 243,547

[22] Filed: Mar. 13, 1981

[51] Int. Cl.³ .................. G01N 33/58; G01N 23/06; B65D 71/00

[52] U.S. Cl. .................. 436/527; 436/529; 436/530; 436/531; 436/541; 436/542; 436/810; 436/824; 422/61; 422/71; 422/57; 422/59

[58] Field of Search .................. 424/1, 105, 12; 23/230 B; 422/61, 68, 69, 70, 71, 57, 59; 436/527, 529–531, 541, 542, 810, 824

[56] References Cited

U.S. PATENT DOCUMENTS

| | | | |
|---|---|---|---|
| 3,975,162 | 8/1976 | Renn | 424/1 |
| 4,053,284 | 10/1977 | Posch | 424/1 |
| 4,065,383 | 12/1977 | Skare et al. | 23/230 B |
| 4,087,248 | 5/1978 | Miles | 424/1 |
| 4,116,638 | 9/1978 | Kenoff | 424/1 |
| 4,123,509 | 10/1978 | Banik et al. | 424/12 |
| 4,160,803 | 7/1979 | Potts | 422/61 |
| 4,166,102 | 8/1979 | Johnson | 424/1 |
| 4,205,058 | 5/1980 | Wagner et al. | 422/61 |
| 4,231,989 | 11/1980 | Thoma | 422/63 |
| 4,244,694 | 1/1981 | Farina et al. | 424/1 |
| 4,254,082 | 3/1981 | Schick et al. | 422/61 |
| 4,268,270 | 5/1981 | Gabbay et al. | 422/61 |
| 4,301,139 | 11/1981 | Feingers et al. | 424/1 |
| 4,315,890 | 2/1982 | Tamers | 422/61 |

*Primary Examiner*—Christine M. Nucker
*Attorney, Agent, or Firm*—Chris H. Morgan

[57] ABSTRACT

A method and device for assaying a test substance utilizing a primary absorbent substance for selectively allowing only a quantity of an analytical reagent proportional to the quantity of test substance to pass therethrough when test substance and analytical reagent are contacted with the primary absorbent. An analytical absorbent is disposed in a series of zones for sequentially absorbing the analytical reagent which passes through the primary absorbent so that detection of the last zone of absorbed analytical reagent indicates the quantity of test substance. The method comprises passing test substance and analytical reagent through the primary absorbent and then the analytical absorbent followed by detection of the last zone in which analytical reagent is absorbed. The device comprises a funnel with the primary absorbent therein for directing the test substance and analytical reagent to a narrow tube holding the analytical absorbent.

40 Claims, 4 Drawing Figures

| POSITIVE | NEGATIVE |
|---|---|
| TEST SUBSTANCE (TS) + ANALYTICAL REAGENT (AR) | FLUID W/O TEST SUBSTANCE + ANALYTICAL REAGENT (AR) |
| ↓ | ↓ |
| BINDER FOR (TS) AND (AR) | BINDER FOR (TS) AND (AR) |
| (AR) IN PROPORTION TO AMOUNT OF (TS) BOUND | NO (AR) |
| INDICATES AMOUNT OF (AR) ↓ | INDICATES NO (AR) ↓ |
| COLUMN OF ANALYTICAL ABSORBENT | COLUMN OF ANALYTICAL ABSORBENT |
| FIG. 3 | FIG. 4 |

ASSAY METHOD AND DEVICE

BACKGROUND OF THE INVENTION

1. Field of the Invention

This invention relates in general to devices and methods for determination of substances and more particularly to methods and devices for assays of binding or bindable substances. Still further, this invention relates to methods and devices for quantitative assays of such binding or bindable substances.

2. Description of the Prior Art

In the past many tests have been provided for determination of binding and bindable substances of various types. Examples of such binding and bindable substances and the substances bound thereto or thereby are antibodies-antigens and other binding proteins-protein bindable substances.

An example of a particular type of demonstration or detection process (assay) used in the past is described in U.S. Pat. No. 3,654,090 to Schuurs et al. This patent describes a test for determination of either an antigen or an antibody. In one example of the 3,654,090 patent, a quantity of antigen is attached to an enzyme and a quantity of antibody is insolubilized by attachment to an insoluble carrier. The enzyme-labelled antigen and the insolubilized antibody are mixed with an unlabeled antigen (the assay substance). By controlling the amount of insolubilized antibody and enzyme-labeled antigen, some or all of the enzyme-labelled antigen is not attached to antibody when unlabeled antigen is present. Some or none of the enzyme-labelled antigen is attached. After mixing, the insoluble material is separated from the soluble material which includes any unattached enzyme-labelled antigen. Centrifuging or washing the insoluble material achieves this separation. An enzyme-reactive agent is then added to either the insoluble or soluble portions to assay the enzyme activity. In this manner, the presence of unlabeled antigen (the assay substance) is determined.

U.S. Pat. No. 3,791,932 to Schuurs et al. describes a similar process for assaying either a binding protein or a substance which is specifically bound by such a protein. In this assay method one of these components is insolubilized and then mixed with the component to be determined, binding the protein to its complement. Next, the solid phase of the insoluble form is separated and reacted with a coupling product of the substance to be determined with an enzyme; i.e., an enzyme-labelled component is mixed with the solid phase such that the enzyme-labeled component will also be bound. The presence of the component to be determined in the first mixing step will prevent coupling of the coupling product (enzyme-component) with at least some of the insolubilized binding components. Determination of the enzyme activity of either the solid or liquid phase resulting from the last mixture will determine the presence of the described components. U.S. Reissue Pat. No. 29,169 is related to U.S. Pat. No. 3,791,932.

Other patents showing similar processes for the determination of binding or bindable substances are shown in U.S. Pat. Nos. 3,839,153 to Schuurs, et al.; 3,850,752 to Schuurs, et al; and 4,016,043 to Schuurs, et al. Each of these patents are similar in that one component is labeled with an enzyme and the other is made insoluble. After mixing the labelled component, the insoluble component and an unlabeled, to be determined, component, the soluble component is separated and the enzyme activity of either the soluble or insoluble portions determines the presence of the unlabeled component.

As described in U.S. Pat. No. 3,966,897 to Renn et al. the same types of competitive and non-competitive bio-assay processes have been performed by radioactively labeling the component instead of enzyme labeling the component. In this type of assay radioactivity is measured instead of enzyme activity. As also described in the 3,966,879 patent, indicator dyes can be attached to the components and then directly measured by visual examination, fluorimetry, spectrophotometry, refractometry or the like. Many of these tests utilize refractive index or radiation intensity or quantitatively measure the assay.

All of these assay procedures involve the reaction of a test substance with an appropriate reagent, for example, hormone-antibody, antigen-antibody, enzyme-substrate, or their converse reactions, together with direct or indirect quantitative measurement of the amount of reagent so reacted by the measurement of a characteristic of a reagent (or of another substance, an indicator, which has reacted with the reagent) such as color, radioactivity, or other physical characteristics.

As shown in U.S. Pat. No. 3,966,897 to Renn et al., in some instances the reagent is immobilized or fixed to a medium into which test substances can be diffused. In the Renn et al. patent, test substance is diffused into a gel medium in which reagent is immobilized against diffusion. One way of immobilizing the reagents in the gel is by absorbing the reagent onto talc, porous glass beads, hydroxyapatite, zirconyl phosphate, charcoal polyethylene, polypropylene, polystyrene particles or the like. After binding the reagent to such a material a conventional assay using a labeled material is obtained by first diffusing test substance into the reagent zone and then using indicators for reacting with the remaining unattached reagent. After excess indicator has been removed, determination of the attached indicator completes the assay.

U.S. Pat. Nos. 3,527,712 to Renn et al. and 3,975,162 to Renn describe processes for applying reagents to mediums such as described in the 3,966,897 patent and preparing gels for use in such mediums.

U.S. Pat. No. 3,654,084 to Moelker describes a process for preparing stable, water-soluble enzyne conjugates.

In the past, avidin and biotin have been coupled with various antigens and antibodies for the purpose of further coupling these antigens and antibodies to other components which could not otherwise be coupled thereto. This has produced antigen or antibody coupling products specific for two or more normally unrelated components.

A particular problem with the assay methods and apparatus which have been used in the past is that they require washing, centrifuging or other separation techniques for separating an insolubilized component from a labeled component. This requires extensive time and labor. Also, equipment for automatically centrifuging and washing a large number of test pieces is expensive. Other test equipment utilized in these past assay methods has been complex and expensive as well.

Another problem with assay methods and devices used in the past is that they are not portable. Thus, field testing has not been easily accomplished. Additionally, most devices for assays have not been simple to assemble or use. Only experts can, therefore, perform most of these assays. Furthermore, most assay chemicals and devices do not have a long shelf life and require expert mixing or preparation.

Still another problem with assay methods and devices used in the past is that they have not been quantitatively accurate, or if quantitatively accurate, the procedure has been complex and requires extensive detection equipment. This is because most quantitative assays are performed by measuring radiation intensity or refractive index.

SUMMARY OF THE INVENTION

The assay method and device of the present invention are significant improvements over the prior art and it is an object of the present invention to provide improved assay methods and devices, especially with regard to the above-mentioned problems.

This invention provides a device for assaying a test substance. This test substance must be capable of being bound by a primary absorbent substance. Also, the primary absorbent substance must be capable of selectively absorbing an analytical reagent such that the presence or absence of test substance with a predetermined quantity of primary absorbent substance and analytical reagent will prevent some analytical reagent from being bound by the primary absorbent substance. The analytical reagent must be capable of being bound by an analytical absorbent substance. The analytical reagent also must be capable of detection once bound by the analytical absorbent substance. Examples of test substances, primary absorbent substances, analytical reagents, and analytical absorbent substances are set forth below.

In accordance with the present invention, a device for assaying a test substance comprises a first fluid conducting means having a first opening for receiving fluid therethrough. A predetermined quantity of primary absorbent substance is fixed to a support means disposed in the first fluid conducting means and retains the primary absorbent substance disposed for contacting fluid passing through the first fluid conducting means. A second fluid conducting means is connected for receiving fluids from the first fluid conducting means. An analytical absorbent substance is supported by a second support means disposed in the second fluid conducting means. The second support means retains the analytical absorbent substance within the second fluid conducting means. Means for detecting the analytical reagent absorbed by the analytical absorbent substance is provided.

Preferably, the second support means supports the analytical absorbent substance in a series of continuous or discontinuous zones through which the fluid sequentially passes such that analytical reagent is sequentially bound therein as it passes therethrough. A predetermined quantity of analytical absorbent is disposed in each zone for binding only a predetermined quantity of analytical reagent. In this manner, detecting the last zone in which analytical reagent is bound indicates the quantity of analytical reagent absorbed in the secondary support means. By controlling the predetermined quantity of primary absorbent substance present in the first fluid conducting means with respect to quantity of analytical reagent contacted with the primary absorbent substance, or vice versa, the quantity of analytical reagent sequentially absorbed in the second fluid conducting means is proportional to the quantity of test substance contacted with the primary absorbent substance. By this means, a device for quantitatively assaying for a test substance is provided.

In the method of the present invention an assay for a test substance comprises steps utilizing the substances described above. First, a predetermined quantity of analytical reagent and a test substance is conducted through and contacted with a predetermined quantity of primary absorbent substance such that the presence or absence of test substance will cause a quantity of analytical reagent not to be bound by the primary absorbent substance. Second, any analytical reagent not bound by the primary absorbent substance is received by and contacted with an analytical absorbent substance binding the analytical reagent to the analytical absorbent substance. The presence of analytical reagent bound to the analytical absorbent substance is then determined.

Preferably, the analytical reagent is sequentially conducted through a series of zones containing predetermined quantities of analytical absorbent and the quantity of bound analytical reagent is determined by detecting the last zone in which analytical reagent is bound. As described, this method can provide a quantitative assay for test substance.

For a further understanding of the invention and further objects, features and advantages thereof, reference may now be had to the following description taken in conjunction with the accompanying drawings.

DESCRIPTION OF PREFERRED EMBODIMENTS

In assaying for a test substance, the present invention utilizes a primary absorbent substance, an analytical reagent substance, and an analytical absorbent substance. Each of these substances are specifically related to each other and to the test substance. Furthermore, each must have certain properties in order for the assay and the assay device to function.

The test substance must be capable of being specifically bound by the primary absorbent. It must also be capable of being bound by the primary absorbent in such a way that, when mixed with a specific amount of primary absorbent and a specific amount of analytical reagent, some of the analytical reagent will or will not be bound. The amount of analytical reagent bound or not bound should be proportional to the amount of test substance mixed with the primary absorbent and analytical reagent.

The analytical reagent must be capable of being specifically bound by a primary absorbent or by a primary absorbent to which test substance is bound. It must also be capable of being specifically bound by an analytical absorbent. The analytical reagent must be capable of being bound by the primary absorbent in such a way that, when a specific amount of analytical reagent is mixed with a specific amount of primary absorbent and at least some test substance, some of the analytical absorbent will or will not be bound by the primary absorbent. The analytical reagent must also be capable of detection once bound by the analytical absorbent. Preferably, the analytical reagent is bound by the analytical absorbent in a very fast reaction so that a distinct and accurate sequential zone measurement can be detected after binding. The sequential zone measurement of analytical absorbent is described in more detail below.

The primary absorbent must be capable of specifically binding test substance as described above. It must also be capable of specifically binding analytical reagent or capable of binding analytical reagent when test substance is attached thereto. The amount of analytical reagent bound or not bound should be proportional to the amount of test substance mixed with the primary absorbent.

In the assay device of the present invention, the primary absorbent should be fixed in a specific location such that analytical reagent and test substance can pass through and be contacted with the primary absorbent.

The analytical absorbent must be capable of specifically binding analytical reagent. And, in the assay device the analytical reagent should be fixed in a specific location. Preferably predetermined quantities of the analytical reagent should be fixed in a series of zones through which fluid sequentially passes such that analytical reagent will be sequentially bound in the zones.

There are a wide variety of substances which meet the requirements described above. There are also a wide variety of well-known processes for producing these substances.

Substances which meet the requirements for a test substance include antigens, antibodies, and various other organic substances. Since the most important requirement of the test substance is that the test substance be capable of being specifically bound by a primary absorbent, those skilled in the art will recognize that a primary absorbent for specifically binding most substances can be prepared.

A wide variety of primary absorbent substances having the properties described above, are possible. Of course, the primary absorbent will depend upon the test substance which must be bound by the primary absorbent. Thus, primary absorbents for antigens or organic molecules assays would include antibodies and lectons specific for the molecule to be assayed. For example, antibodies against specific microbial antigens, proteins, hormones, polysaccharides, antibodies, toxins, etc. could be used for a primary absorbent substance. Also, lectins with specific binding activity for sugars, enzyme co-factors, polysaccharides, etc. could be used. Primary absorbent substances for antibody assays could include antigens or organic compounds for which the antibody is specific. For example, microbial antigen, protein, hormones, polysaccharides, antibiotic, toxin, etc. having specific binding activity with the antibody to be assayed could be used.

A wide variety of chemicals can also be used for analytical reagents. One simple way of preparing an analytical reagent is to utilize the substance which is being tested for by labeling the test substance chemical with a detectable group and with a group capable of binding specifically to the analytical absorbent. For example, if the test substance is an antibody, the antibody can be coupled to an enzyme for detection and also coupled to biotin for specifically binding to an avidin analytical absorbent.

Of course, wide variety of detectable groups can be coupled to particular compounds in forming the analytical reagent. These detectable or indicator groups include colored dye, enzymes, fluorescent compounds, radioisotopes, and others. Particular enzymes include horse radish peroxidase, alkaline phosphate, B-galactosidase and others. Examples of colored dyes are amido black, and eosin. Fluorescent compounds include fluorescein isothiocyanate, dansyl, and others. Radioisotopes include Carbon 14 and Iodine 125 and others. Of course, the detectable group most desirable depends upon the particular assay and the particular device being utilized for the assay.

The group coupled to the analytical reagent capable of specifically binding to the analytical absorbent depends upon the analytical absorbent. Examples of binding groups capable of binding specifically to the analytical absorbent are biotin; avidin; antigen; enzyme substrate analogues; antibody; 2,4-dinetrophenol (specific for MOPC-315 mouse myeloma protein); and enzyme. Compounds to which the compounds described above are bound, can include antibodies, antigens, organic molecules and lectins. The antibodies may be conventional antibodies or they may be monoclonal antibodies specific against microbial antigens, proteins, polysaccharides, antibiotics, toxins, hormones, etc. The antigens may be microbial antigens, proteins, polysaccharides, antibiotics, toxins, hormones, etc. The organic molecules include all of those capable of specific binding to lectin.

While a preferred method of forming the analytical reagent is to couple groups to a compound with the same specificity as the material being assayed with respect to the primary absorbent, this is not an absolute requirement. As described in more detail below, the analytical reagent may have specific binding activity with the test substance and not the primary absorbent alone. In this instance, the analytical reagent will pass through the primary absorbent if no test substance is coupled thereto.

The methods for coupling detectable groups and analytical absorbent groups to various compounds are well known in the art. Examples of preparation methods for preparing analytical reagent include:

I. m-maleimidobenzoyl-N-hydroxysuccinimide ester coupling of beta-galactosidase to either antigen or antibody:

a. In this procedure, if antigen is to be coupled to the enzyme, then antibody is first covalently bonded to an insoluble support. If antibody is to be coupled to enzyme then antigen is covalently bonded to an insoluble support (see procedure for coupling chemicals to supports, below). This procedure results in a Primary Absorbent utilized as a base for unidirectional coupling and preventing crosslinking of reagents.

b. After the Primary Absorbent is prepared, it is washed thoroughly with glycine or tris buffer, pH 7.2., 0.1 M.

c. The antigen or antibody to be coupled is then added to the Primary Absorbent and allowed to indicate overnight at 4° C. to allow antigen-antibody reaction to occur.

d. The Primary Absorbent is again washed with buffer as in (b) above, followed by washing with pH 7.2, 0.1 M phosphate buffer containing 0.01 M magnesium chloride (PBS-M).

e. Sufficient iodoacetamide is then added to the Primary Absorbent to bring the final concentration to 0.01 M (this step is to block any free sulfhydril groups present on the Primary Absorbent or coupled antigen or antibody) and the mixture is incubated with stirring for 1 hour at room temperature.

f. The Primary Absorbent is again washed with PBS-M.

g. m-maleimidobenzoyl-N-hydroxysuccinimide ester is added to the Primary Absorbent to a final concentration to 0.01 M and allowed to incubate at room temperature with stirring for two hours.

h. The Primary Absorbent is again washed with PBS-M.

i. Add 500 iu of beta-galactosidase for each 20 ml. packed volume of Primary Absorbent and incubate the mixture at 4° C. overnight, mixing periodically.

j. The Primary Absorbent is again washed with PBS-M.

k. The antigen or antibody coupled to beta-galactosidase is then eluted from the Primary Absorbent by electrophoresis in a 3 cm vertical column in glycine, 0.01 M, pH 2.5 containing 0.005 M $MgCl_2$, 3 hours, 10 ma. (the electrophoresis column is equipped with a porous disk to support the Primary Absorbent and a dialysis membrane 3 cm below the disk toward the cathode to trap the eluted material).

II. Glutaraldehyde coupling of peroxidase to antigen or antibody:

a. For each 10 mg of antigen or antibody suspended in pH 7.2, 0.1 M phosphate buffer (PB) 500 iu of peroxidase are added.

b. 5 ml of freshly prepared 0.25% glutaraldehyde solution are added and the mixture is stirred at 4° C. for 2 hours.

c. The mixture is dialysed against 2000 volumes of PB at 4° C. for 12–18 hours.

d. The mixture is centrifuged at 5000×g for 30 minutes fo remove large aggregates.

III. m-maleimidobenzoyl-N-hydroxysuccinimide ester coupling of beta-galactosidase to either antigen or antibody using a cleavable bond to immobilize antigen or antibody:

a. In this procedure, antigen or antibody is coupled to an insoluble support containing a free amino group by treating the support with citraconic anhydride for 2 hours at room temperature.

b. Washed thoroughly with phosphate buffer (PB), pH 7.2, 0.1 M.

c. The antigen or antibody to be coupled is then added to the activated support and allowed to incubate overnight at 4° C.

d. The support is again washed with buffer as in (b).

e. Sufficient iodoacetamide is then added to the support to bring the final concentration to 0.01 M (this step is to block any free sulfhydryl groups present on the Primary Absorbent or coupled antigen or antibody) and the mixture is then incubated with stirring for 1 hour at room temperature.

f. The support is again washed with PB.

g. m-maleimidobenzoyl-N-hydroxysuccinimide ester (MBS) is added to the support to a final concentration of 0.01 M and allowed to incubate at room temperature with stirring for 2 hours.

h. The support is washed with PBS-M.

i. Add 500 iu of beta-galactosidase for each 20 ml packed volume of support and incubate the mixture at 4° C. overnight, mixing periodically.

j. The support is again washed with PBS-M.

k. The antigen or antibody coupled to beta-galactosidase is then eluted from the support with pH 10 phosphate buffer, 0.01 M containing 0.01 $MgCl_{12}$ (citraconic anhydride is cleaved at pH 10).

IV. Coupling antigen or antibody-Enzyme Comples to biotin isothiocyanate (FITC):

a. Suspend 10 mg of d-biotin in 10 ml of N,N-dimethyl formamide.

b. Add 10 mg of dicyclohexylcarbodiimide and stir the mixture for 2 hours at room temperature.

c. Add the activated (-COOH group activated) d-biotin mixture to an aqueous solution (PB) containing the antigen/antibody enzyme (Dicyclohexylcarbodiimide is insoluble in water and does not cross-link).

d. Incubate the mixture at 4° C. for 12–18 hours while stirring.

e. Dialyze the mixture against 2000 volumes of PB at 4° C. for 12–18 hours.

Other methods of coupling desired groups to compounds are well known to those skilled in the art and can be used to prepare the same or other analytical reagents.

V. Coupling Antigen or Antibody to Fluorescein Isothiocyanate (FITC)

a. FITC is dissolved (1 mg/ml) in 0.15 m sodium phosphate buffer pH 9.0.

b. 1 ml of FITC solution is added to each 4 ml containing 100 mg of antigen or antibody.

c. Adjust pH to 9.5 and incubate at room temperature for 1 hour with mixing d. Remove excess FITC by chromatography through sephadex G-25.

Compounds suitable as analytical absorbents include avidin, biotin, antigen, antibody, enzyme, enzyme substrate analogue, myeloma proteins and other binding proteins. A particularly useful analytical absorbent consists of either avidin or biotin. Avidin couples to biotin with a very fast coupling rate. Also, avidin and biotin are widely available and relatively inexpensive. Still further, avidin and biotin can be readily coupled to various types of supports and to many other components.

Figure 1:
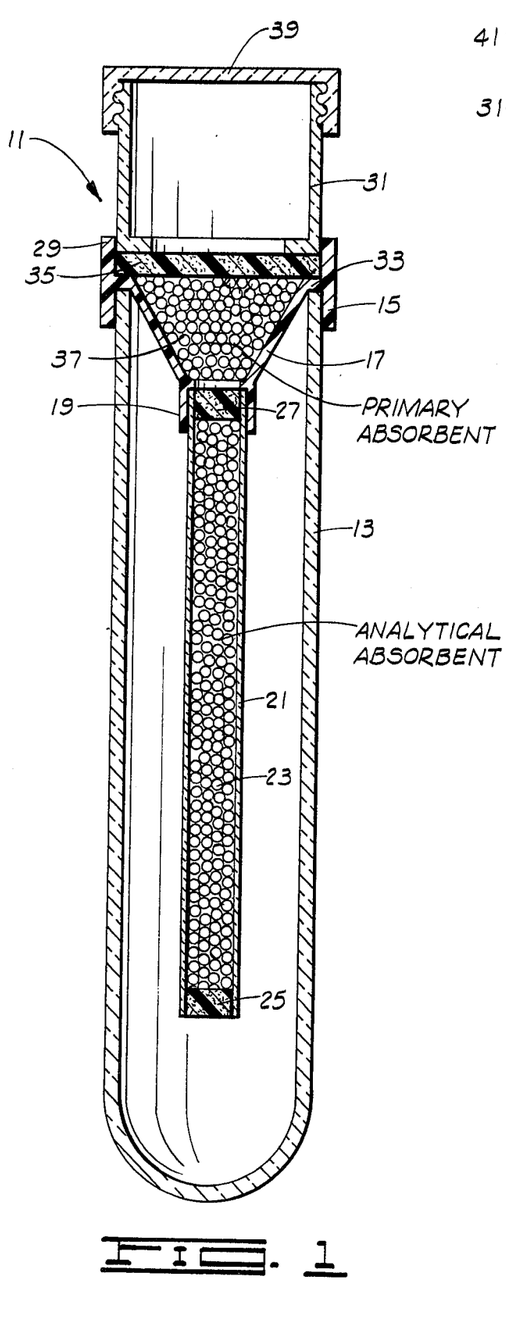
FIG. 1 is a cross-sectional view of an assay device of the present invention.
Figure 2:
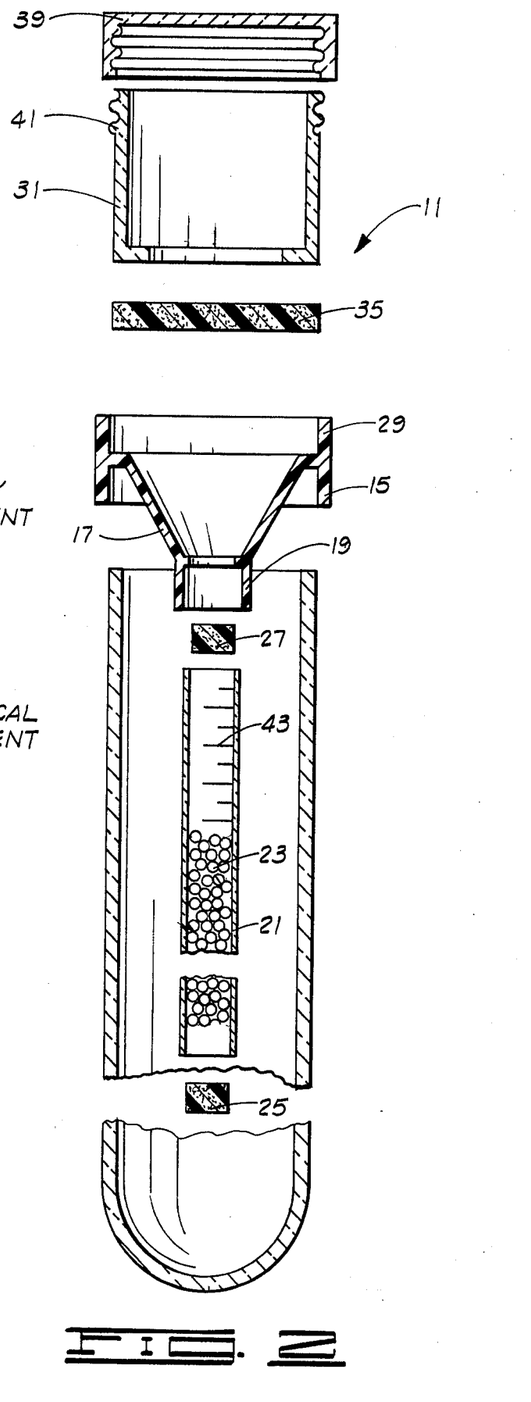
FIG. 2 is an exploded cross-sectional view of the assay device shown in FIG. 1.

Referring now to FIGS. 1 and 2, an apparatus in accordance with the present invention is shown generally at 11. The apparatus 11 consists of a clear glass test tube 13 having an opening at its upper end. The top of tube 13 is press-fitted into a lip which extends downwardly from the upper rim of a funnel 17. The funnel 17 extends downwardly into the tube 13 and has a cylindrical receptacle 19 at its lower end. The cylindrical receptacle 19 receives, press-fitted therein, a clear glass capillary tube 21. The capillary tube 21 is filled with a plurality of glass beads 23. These glass beads 23 fixedly support the analytical absorbent within the capillary tube 21 for contacting fluid passing through the capillary tube 21. A plug 25 is press-fitted into the lower end of capillary tube 21 to retain the beads 23 within the tube 21. A plug 27 is press-fitted into the upper end of the capillary tube 21 to retain the beads 23 within tube 21 when inverted.

The capillary tube 21 is held suspended inside test tube 23 by funnel 17. Fluid passing through capillary tube 21 will pass into and be retained by test tube 13. The beads 23 and the interior of capillary tube 21 are visible through the walls of test tube 13 and capillary tube 21.

Extending from the upper rim of funnel 17 is a lower cylindrical lip 15 and an upper cylindrical lip 29. These lips extend axially. The lower lip 15 receives the upper end of glass tube 13 and extends outside test tube 13 with tube 13 press-fitted therein. If desired, glue or the like can permanently bond tube 13 to funnel 17. Upper lip 29 receives a cup 31. Cup 31 has the same cylindrical diameter as tube 13. The cup 31 is pressfitted into the upper cylindrical lip 29 in the same manner as tube 13 is press-fitted into the lower cylindrical lip 15.

Cup 31 is disposed above a shoulder rim 33 of funnel 17 extending inwardly between lip 25 and lip 27. Cup 31 has openings in its upper end and its lower end. The interior of funnel 17 between plugs 27 and 35 is filled with a plurality of glass beads 37. The beads 37 fixedly support the primary absorbent for contacting fluid passing through funnel 17.

The plugs 25, 27 and 35 are each made of a porous material such as polypropylene which fluid can readily pass but firmly retaining the beads within funnel 17 and tube 21. Plug 27 separates the beads 37 and the beads 23.

If desired, cup 31 and plug 35 can be fused or glued to funnel 17 to permanently hold them in position.

A threaded cap 39 is received by threads 41 at the upper end of cup 31. Cap 39 closes the upper end of cup 31 and prevents foreign matter from inadvertently entering the assay device.

As can be seen, the construction of the device 11 provides a specific fluid conducting passageway such that fluid enters through the top of cup 31, passes through plug 35 and contacts beads 37, through plugs 27 into capillary 21 contacting beads 23, and then passes through the plug 25 and into tube 13. As described below, it is important that the fluid be first intimately contacted with and passed through beads 37 prior to being conducted through capillary 21. It is also important that capillary 21 be a relatively narrow path. This allows sequential binding to the beads 23 and the analytical absorbent. By arrangement of the beads in zones and by loading these zones with predetermined amounts of analytical absorbent, sequential binding of analytical reagent can be quantitatively determined by the last zone in which binding occurs.

If desired, graduation marks 43 can be placed on the capillary tube 21 to allow visual examination and determination of the length of linear reaction (or the last zone in which binding of analytical reagent has occured) within the tube. Also if desired, a small hole can be provided through funnel 17 or tube 13 to allow air to escape as liquid enters tube 13 through capillary 21.

As described above, beads 23 and 37 support the primary absorbent substance and analytical absorbent, respectively. Beads are utilized because they insure that fluids passing therethrough will have an intimate contact with the absorbent substance disposed thereon. It is also relatively easy to attach absorbent substance to beads so that the respective absorbent substance will not escape funnel 17 and capillary tube 21.

While FIGS. 1 and 2 show the primary absorbent substance and analytical absorbent being supported on glass beads, other materials can be used as supports for these substances. These supports can include membrane filters such as cellulose acetate, or cellulose acetate-nitrate; glass fiber filters; or beads made or agarose, cellulose, dextran, polyacrylamide, etc. In fact, no separate support would be required if a sufficiently narrow tube is utilized and the absorbent is attached to the inner wall of the tube. The main feature of the support material is that it provides intimate contact between the absorbent substance attached thereto and the fluid passing through the fluid passageway.

As depicted in FIGS. 1 and 2, the capillary tube 21 is slightly oversized to make clear its detail. Normally, the interior diameter of the capillary tube is approximately 0.5 to 2 mm. The glass beads 23 and 37 each have a diameter of approximately 0.01 to 5 mm. The diameter of the capillary tube 21 and the diameter of the glass beads each depends upon the density of the absorbent, the desired sensitivity of the quantitative measurement, and the desired flow rate for fluid through the capillary 21.

Several methods for coupling chemicals to supports can be used depending upon the chemical composition of the support and the chemical to be attached to the support. These methods include cyanogen bromide coupling, silation, diazo coupling, carbodiimide coupling and gluteraldehyde coupling.

In cyanogen bromide coupling, proteins and polysaccharides can be coupled onto supports such as cellulose filters, cellulose acetate/nitrate filters, nylon filters, agarose beads, cellulose beads, and polyacrylamide beads. It can also be used for the introduction of spacer groups such as diamino alkyl or aryl, or gamma amino alkyl or aryl carboxylic acid onto the support. Briefly, the sequence of reaction is as follows:
  a. For each 20 g of support in 50 ml of water, dissolve 10 g of CNBr in 100 ml of water and add slowly to support, maintaining temperature at 4°-6° C. and pH at 10-11 by adding 4 N NaOH. Activation is complete in approximately ten minutes.
  b. Wash support by filtration using cold 0.1 M bicarbonate buffer, pH9.
  c. The activated support is added to the material to be coupled (protein, polysaccharide, diamine, gamma-amino carboxylic acid, etc.) dissolved in 0.1 M bicarbonate buffer, pH 9, and allowed to react at 4° C. for 12-18 hours.
  d. The coupled support is washed by filtration with either 0.1 M glycine buffer or 0.1 M TRIS buffer, pH 7.2 (these buffers block any remaining CNBr sites).

For silation of glass supports such as glass fiber filters, glass beads, glass capillaries, etc., various triethoxysilanes and trimethoxysilanes may be used. For example, gamma-aminopropyltriethoxysilane or N-(B-aminoethyl-gamma-aminopropyl) trimethoxysilane as spacer groups attached to glass as follows:
  a. A 10% solution to the triethoxy- or trimethoxy-silane is prepared in water, pH 4.
  b. The support is added to the solution and reacted at 60°-70° C. for 3 hours.
  c. The solution is removed by filtration and the support is incubated for 12-18 hours at 125° C.
  d. The support is washed by filtration with acetone followed by water to remove excess silane.

Diazo coupling of proteins and other amine containing organic molecules to spacer groups on supports may be achieved as follows:
  a. The amine of the spacer (only spacers with aryl amines may be diazotized) is converted to a diazonium chloride group by treatment with a solution containing 0.1 M $NaNO_2$ and 0.1 M HCl for 12 hours at 15°-16° C. temperature.
  b. Wash the support with water by filtration.

c. Dissolve the protein or amine (tyrosine) containing molecule in 0.05 M phosphate buffer, pH 8-9 and add to the support.
d. Incubate at 4° C. for 12-18 hours.
e. Wash by filtration with cold 0.5 M glycine buffer containing 0.15 M NaCl, pH 7.2.

Carbodiimide coupling of other proteins and other amine containing organic molecules to spacer groups on supports may be achieved as follows:
 a. Convert the terminal amine of the support bound spacer to a carboxylic acid by treatment with a solution containing 9.5 M succinic anhydride by incubation at 25° C. for 12-18 hours, maintaining pH 7-8.
 b. Wash by filtration with water.
 c. Treat the support bound carboxylic acid spacer with 0.1 M 1-(3-dimethylaminopropyl)-3-ethylcarbodiimide at pH 5, 4° C., for 4 hours.
 d. Wash by filtration with water.
 e. Dissolve the protein or amine containing molecule in 0.1 M phosphate buffer containing 0.15 M NaCl, pH 5, and add to the support.
 f. Incubate at 4° C. for 12-18 hours.
 g. Wash by filtration with 0.5 M glycine buffer containing 0.15 M NaCl, pH 7.2.

Carbodiimide coupling of organic molecules containing carboxyl or aldehyde groups to spacer groups on supports may be achieved as follows:
 a. Suspend the support bound spacer in a solution containing 0.1 M 1-(3-dimethylaminopropyl)-3-ethylcarbodiimide.
 b. Dissolve the organic molecules in 0.15 M NaCl, pH 5 and add to the support mixture.
 c. Incubate at 4° C. for 12-18 hours.
 d. Wash by filtration with cold 0.5 M glycine buffer, pH 7.2.

Gluteraldehyde coupling of proteins and other amine-containing molecules to spacer groups on supports may be achieved as follows:
 a. Treat the support bound spacer groups with a freshly prepared solution containing 0.5% glutaraldehyde in water for 20 minutes at room temperature.
 b. Wash by filtration with water.
 c. Add the support bound spacer to a solution containing the protein or molecules to be coupled in 0.15 M NaCl.
 d. Incubate at room temperature for 2 hours.
 e. Wash by filtration with a cold solution containing 0.5 M glycine and 0.15 M NaCl, pH 7.2.

To perform an assay in accordance with the method of the present invention an apparatus as described above can be utilized. A predetermined quantity of primary absorbent is attached to the beads 37. Also, a predetermined density of analytical absorbent is prepared through the column of glass beads 23 in capillary tube 21. The primary absorbent and the analytical absorbent are prepared specifically for a particular test substance and analytical reagent. A predetermined amount of analytical reagent is prepared for use with the apparatus. For this description, the analytical reagent is of a type specifically bound by a primary absorbent so that analytical reagent competes with test substance for being bound by the primary absorbent.

Figure 3:
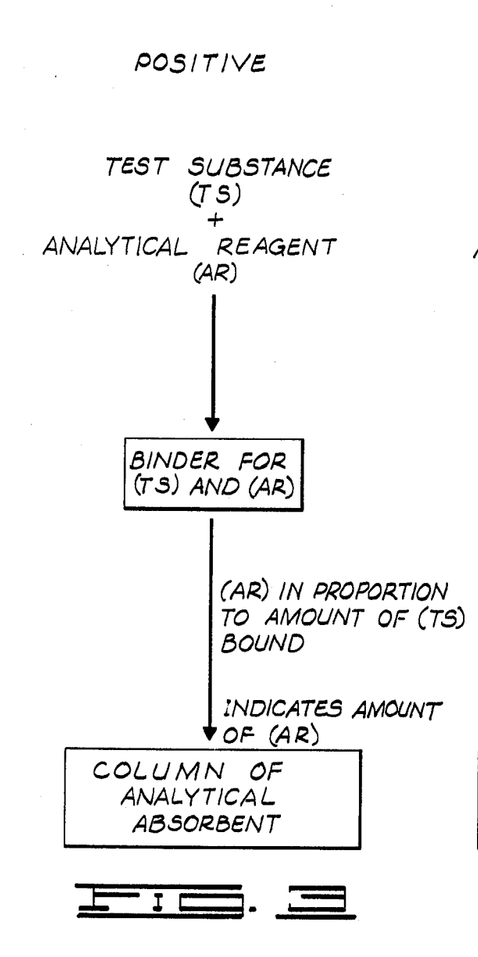
FIG. 3 is a schematic representation of an assay method in accordance with the present invention.
Figure 4:
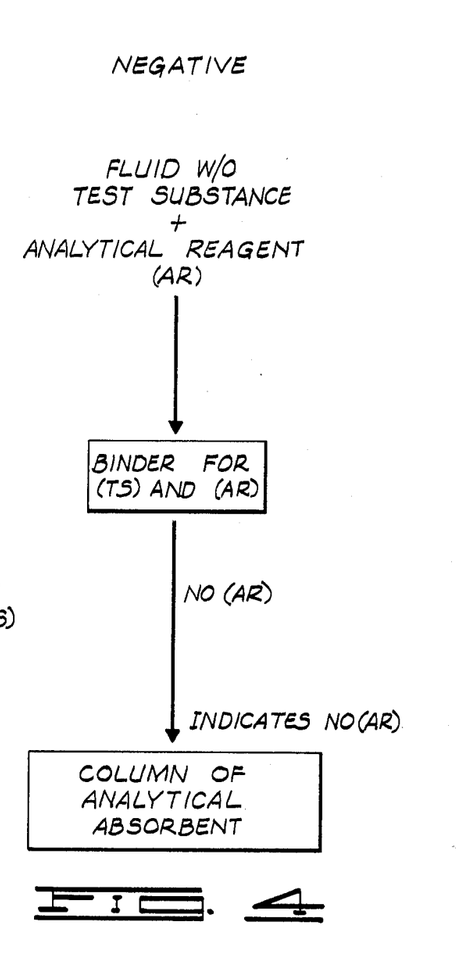
FIG. 4 is a schematic representation of an assay method in accordance with the present invention.

Referring now to FIGS. 3 and 4 as well as FIGS. 1 and 2, the method of assaying can be more clearly undersood. First, a specific quantity of fluid to be assayed for test substance is mixed with a predetermined quantity of analytical reagent. This mixture is then poured into cup 31. The test substance and the analytical reagent pass through and contact the primary absorbent substance held on beads 37. If test substance is present in the assay fluid, some of the analytical reagent will not be bound by the primary absorbent and will pass through the beads 37 and into the capillary tube 21. The amount of analytical reagent which passes through the beads 37 into the tube 21 is proportional to the amount of test substance bound by the primary absorbent. Of course, the specific amounts of primary absorbent on beads 37 and the amount of analytical reagent mixed with the assay fluid is carefully balanced to insure that no analytical reagent will pass through the beads 37 if no test substance is present, and, at the same time, at least some analytical reagent will pass through the beads 37 if test substance is present in the assay fluid.

If analytical reagent passes through the beads 37 and the primary absorbent it will enter capillary tube 21 and be bound by the analytical absorbent substance disposed on the beads 23 therein. If the binding reaction between analytical reagent and analytical absorbent is sufficiently fast, the binding of analytical reagent will occur linearly down the column of analytical absorbent. For example, if only enough analytical reagent is present to bind one third of the analytical absorbent in the capillary tube 21, all of the binding will occur in the upper one-third of the capillary tube 21. None of the bottom two-thirds of the capillary tube will have any analytical reagent bound therein. If the analytical reagent carries a dye, such as amido black, the quantity of analytical reagent bound, and hence, the quantity of test substance in the assay fluid can be determined by a visual inspection of the capillary tube 21. Of course, the length of the graduated capillary tube colored by the dye must be compared to the density of the analytical absorbent and the proportionality of analytical reagent which is not bound due to the presence of test substance. This relationship can be empirically or analytically determined.

As mentioned above, other methods of detecting the presence of bound analytical reagent in the column of analytical absorbent are possible. For example, if the analytical reagent contains an enzyme, an enzyme reactive agent can be passed through the analytical absorbent tube to assay the enzyme activity. The product of the enzyme reactive agent and the enzyme will be fixed in the column due to the physical size of the openings between the glass beads 23. If a fluorescent compound is utilized in the analytical reagent, the column of analytical absorbent can be surveyed for fluorescence after the analytical reagent is bound. Finally, if radioisotopes are utilized in the analytical reagent, the column of analytical absorbent can be surveyed for the presence of radioisotopes after the analytical reagent has been bound.

In many instances, it will be desirable to utilize enzymes in the analytical reagents because assays of enzyme activity are much more sensitive than most other types of assays.

While the above method describes mixing the analytical reagent with the assay fluid prior to pouring the fluid into cup 31, the fluids need not necessarily be mixed nor is the particular order in which they contact the primary absorbent required. Thus, the analytical reagent could be poured through the beads 37 first followed by assay fluid. The assay could also be performed in reverse order; assay fluid first, analytical reagent second. The order is not critical in most cases because, generally, test substance will displace analytical reagent bound by the primary absorbent if the analytical reagent is bound first. In contrast, generally, test substance will not be displaced by analytical reagent if the test substance is bound first.

In some instances, the order of adding analytical reagent and assay fluid can be important. For example, if the analytical reagent is not specifically bound by the primary absorbent alone, but is only bound by primary absorbent to which test substance has been bound, then the assay fluid must be added first followed by the analytical reagent. Furthermore, in this type of assay, it is the amount of analytical reagent bound by the beads 37 and not bound in the beads 23 which is proportional to the amount of test substance. An example of such an assay is an assay for a specific antibody where the primary absorbent is an antigen specific for this antibody and the analytical reagent is an anti antibody specific for the particular antibody but not for the antigen. In this case, the assay fluid (containing antibody) must be contacted with the primary absorbent (antigen) and then the analytical reagent (anti antibody—detectable substance—substance bound by analytical absorbent) contacted with the primary absorbent. Or at least, the analytical reagent cannot be contacted with the primary absorbent, alone, first.

This concept of binding analytical reagent directly to bound test substance can be utilized to provide a slightly different type of assay. In this assay, since the analytical reagent does not necessarily have to be bound by the primary absorbent alone, the primary absorbent can be of specificity only to the test substance. This would allow even a non-chemical primary absorbent such as filters or the like if the test substance can be bound thereby while allowing the analytical reagent to pass therethrough if no test substance is bound.

As can be seen, the method and device of the present invention provide a quantitative assay much improved over assays which require color determination or intensity determinations. As can be seen, the present invention can be made as sensitive as desired by regulating the linear density of the analytical absorbent as well as the sensitivity of the detection means for the analytical reagent. Extremely sensitive quantitative assays can be performed with enzyme-labeled analytical reagents and fine linear densities of analytical absorbent.

When assaying for a quantity of test substance, it is sometimes desirable to utilize a logarhithmic linear density of analytical absorbent. This is especially true where the unknown quantity can vary over a wide range. By making the density of the analytical absorbent lower at the entrance of the column, and then gradually larger toward the exit of the column, such a logarithmic scale will extend the quantitative measurement over a broader range. One way of providing this varying density is by providing a capillary tube (in place of capillary tube 21) which is narrow at the top and which gradually widens toward its lower end.

Another way of providing a sensitive test while utilizing a straight, linear density is to run successive tests with successively smaller quantities of assay fluid being mixed with the analytical reagent. For example, if the first run of an assay produces a column wherein analytical absorbent is completely bound with analytical reagent a second test can be run utilizing one-tenth the quantity of assay fluid. Successively decreased amounts of assay fluid can be added until only a portion of the analytical absorbent is bound with analytical reagent. The quantitative density of test substance in the assay fluid can be scaled accordingly Although one of the above methods describes adding analytical reagent to the primary absorbent along with assay fluid, it is possible to add the analytical reagent first. However, in many cases, it is not possible to allow the analytical reagent to dry in contact with and be bound by the primary absorbent because, once dried, the test substance will not quickly displace the analytical reagent from the primary absorbent.

As shown above, the present invention and method for assaying do not require washing to separate an insolubilized component from a labeled component. This is because the primary absorbent is fixed on a permeable support. The analytical reagent not bound by the primary absorbent passes through the support material simply by gravity. Of course, suction could be applied to provide a faster flow of the fluid.

Another reason no washing is required is that the analytical absorbent is bound in a separate area and does not need to be remixed in a fluid medium to produce an assay by intensity or refractive index or the like.

The present invention can be used with special advantage with the recently produced hybridoma or monoclonal antibodies. Production of such antibodies is described in U.S. Pat. No. 4,196,265 to Koprowski et al. A particular advantage of monoclonal antibodies is that they are readily produced against specific virus and antigenic determinants. By utilizing the monoclonal antibody as a binding or bindable agent in the present invention, assay methods and devices can be provided which are precisely specific for a particular determinant and are quantitatively accurate as well.

Another distinct advantage of the present invention is that the device is both portable and has a long shelf life. This allows field assays to be accurate in quantity and allows the assay devices to be stored for long periods of time. The portability and long shelf life are provided by the stable chemical binding of the analytical absorbent and primary absorbent on the membranes and beads used as supports. Generally, these chemicals can be allowed to dry without adverse effect. Furthermore, the analytical reagent can be stored separately and will also have a long shelf life.

Thus, the assay method and device of the present invention are well adapted to attain the objects and advantages mentioned as well as those inherent therein. While presently preferred embodiments of the present invention have been described for the purpose of this disclosure, numerous changes in the construction and arrangement of parts can be made by those skilled in the art which changes are encompassed within the spirit of this invetnion as defined by the appended claims. The following examples are provided to still more particularly describe selected embodiments of the invention.

EXAMPLES

I. Primary Absorbent—primary absorbent (coccidiodes immunodiffusion antigen) was attached to glass beads as follows:

a. 0.25 mm glass beads (30 g) were treated with N($\beta$-aminoethyl) $\gamma$-Aminopropyltrimethoxysilane to provide free amino groups, 18 hours at 126° C.

b. The beads were washed two times with acetone.

c. The beads were washed three times with boiling water.

d. The beads were treated thirty minutes with 1% glutaraldehyde.

e. The beads were washed three times with cold, distilled water.

f. The resulting schiff's base beads were then coupled with five ml of coccidiodes immunodiffusion antigen for 4 hours at room temperature.

g. The coupled beads were washed four times with pH 7.2 glycine buffer.

II. Analytical Reagent—an analytical reagent (anticocci-galactosidase-biotin) was prepared using the attached primary absorbent as follows:

a. Anti-Coccidiodes (Goat) 10 ml. were added to beads and were shaken at 4° C. for 18 hours (sensitizing).

b. The coupled-sensitized beads (CSB) were washed four times with PBS (phosphate buffered saline).

c. CSB in 15 ml. of PBS pH 7.2 were treated with 0.1 g Iodoacetamide for 2 hours at room temperature (blocking SH groups).

d. CSB were washed three times with PBS, pH 7.2.

e. CSB in 15 ml of PBS pH 7.2 were treated with 0.1 g of m-Maleimidibenzoyl-N-hydroxysuccinimide ester, for two hours at room temperature.

f. CSB were washed three times with PBS pH 7.2.

g. CSB in 15 ml of PBS, pH 7.2., were treated with 1000 units of B-galactosidase (*E coli.*), for four hours at room temperature (coupling B-galactosidase to antibody).

h. The beads were then washed three times with PBS pH 7.2.

i. The beads were suspended in 15 ml PBS pH 7.2 and treated with 0.1 g d-Biotin-N-hydroxysuccinimide ester for four hours at room temperature.

j. The beads were washed four times with PBS, pH 7.2.

k. A sample of glass beads were tested for B-galactosidase activity by adding 5-Bromo-4-chloro-3-indolyl-B-D-galactoside saturated in PBS pH 7.2 with 0.1% M MgCl. Color change was detected in two minutes.

l. The anti-cocci-B-galactosidase-biotin complex was electro-eluted from the beads in an apparatus using a filter support for the beads and a dialysis membrane below the filter support. Buffer 0.01 m glycine, pH 3.0 was used in the electroelution; 400 V., 80 mA, 3 hours, 4° C. 20 ml. of liquid was present above the dialysis membrane. This was dispensed in 1 ml aliquots and frozen (−20° C.).

III. Analytical Absorbent—an analytical absorbent was coupled to glass beads as follows:

a. 30 g 0.25 mm glass beads were treated with N($\gamma$-Aminoethyl) $\gamma$-Aminopropyl Trimethoxysilane at 125° C. for 18 hours.

b. The beads were washed two times with acetone, three times with boiling water.

c. The beads were suspended in 50 ml. 0.1% glutaraldehyde for one hour.

d. The beads were washed three times with cold, distilled water.

e. The beads were suspended in 15 ml Saline, 0.1 g Avidin added and incubated with shaking for four hours at room temperature.

f. The beads were washed three times with glycine buffer, pH 7.2.

IV. Several apparatus were prepared using the analytical absorbent beads and primary absorbent beads described above. Each of the apparatus consisted of a 15 ml. centrifuge tube with a hole drilled in its lower end to receive a 1 ml. pipette. The analytical absorbent beads were loosely packed into the pipette and the primary absorbent beads were poured into the centitube above the pipette. Testing was first performed to determine density of the analytical absorbent as follows:

a. To separate columns, 0.1, 0.25 and 0.5 ml of analytical reagent (AR) were added to the primary absorbent and incubated for 15 minutes at room temperature.

b. Then, 5 ml of PBS pH 7.2 containing 0.1 Bovine serum albumin (BSA) 0.01 m MgCl2 was added to each column.

c. 5 ml of PBS-A saturated with 5-Bromo-4-chloro-3-indolyl-B-d-galactoside (enzyme substrate) were added to each column and incubated at room temperature with tops sealed when last of the liquid entered bed.

d. Colored zone lengths are as follows:

1. 0.1 ml AR—0 mm zone length
2. 0.25 ml AR—4 mm zone length
3. 0.5 ml AR—7 mm zone length V. Next, testing for quantitative proportionality of zone length was performed by using the following tests:

a. 0.2 ml each of AR were dispensed into 8 tubes and the following amounts of serum known to contain cocci antibodies were added to each tube:

| Tube # | 1 | 2 | 3 | 4 | 5 | 6 | 7 | 8 |
|---|---|---|---|---|---|---|---|---|
| Vol. AR | 0.2 | 0.2 | 0.2 | 0.2 | 0.2 | 0.2 | 0.2 | 0.2 |
| Vol. Ser | — | — | 0.1 | 0.1 | 0.25 | 0.25 | 0.5 | 0.5 | b. The contents of each tube were transferred to separate columns and incubated thirty minutes at room temperature.

c. 5 ml of PBS-A were added to each column and allowed to flow through.

d. 2 ml of enzyme substrate were added to each column, allowed to flow through and the columns sealed. Incubation at room temperature proceeded for one hour.

e. Colored zone measurements were as follows:

| Tube # | 1 | 2 | 3 | 4 | 5 | 6 | 7 | 8 |
|---|---|---|---|---|---|---|---|---|
| Zone Length (mm) | 1 | 0.5 | 3 | 3 | 7 | 10 | 15 | 18 |

As can be seen, slight variations in zone length occurred. These variations were apparently due to dissimilarities of the packing of the beads causing variation in analytical reagent density. Otherwise, the zone length tended to have a linear proportionality to analytical reagent and, hence, test substance.

The foregoing disclosure and the showings made in the drawings are merely illustrative of the principles of this invention and are not to be interpreted in a limiting sense.

What is claimed is:

1. A device for use in assaying a test substance comprising:

a first fluid conducting means having a first opening for receiving fluid therethrough;

a predetermined quantity of primary absorbent substance capable of binding said test substance and interacting with said test substance and an analytical reagent such that a quantity of said analytical reagent proportional to the quantity of said test substance will not be bound by said primary absorbent substance when a predetermined quantity of said analytical reagent and said test substance are contacted with said primary absorbent substance;

a first support means disposed in said first fluid conducting means and to which said primary absorbent substance is attached for retaining said primary absorbent substance disposed for contacting fluid passing through said first fluid conducting means;

second fluid conducting means connected for receiving fluid from said first fluid conducting means;

an analytical absorbent substance for absorbing said analytical reagent;

a second support means disposed in said second fluid conducting means and to which said analytical reagent is attached for supporting a predetermined quantity of said analytical absorbent substance in each of a series of zones within said second fluid conducting means such that as said analytical reagent passes through said second fluid conducting means it is sequentially absorbed within said zones; and means for detecting the last zone in said second fluid conducting means in which analytical reagent is absorbed.

2. The device of claim 1 wherein said primary absorbent substance is selected from the group consisting of: antibodies, antigens, binding proteins, bindable proteins, polysaccharides, antibiotics hormones and toxins.

3. The device of claim 1 wherein said analytical absorbent substance is selected from the group consisting of: avidin, biotin, antigens, antibodies, enzymes, enzyme substrate analogues and myeloma proteins.

4. The device of claim 3 wherein said analytical absorbent substance is a selected one of avidin and biotin.

5. The device of claim 1 wherein said first fluid conducting means comprises a funnel for catching and directing a downwardly flowing fluid to a lower opening in said funnel to which said second fluid conducting means is attached.

6. The device of claim 5 wherein said second fluid conducting means comprises a narrow, transparent tube.

7. The device of claim 6 which further comprises transparent housing means for housing said funnel and said transparent tube and for receiving fluid which drains from said transparent tube.

8. The device of claim 7 wherein said first and second support means comprise beads.

9. The device of claim 8 which further comprises:
a fluid-permeable separator means disposed in said lower opening for separating said beads of said first support means and said beads of said second support means;
a fluid-permeable first holding means disposed across said funnel for retaining said beads of said first support means within said funnel; and
a fluid-permeable second holding means disposed across said transparent tube for retaining said beads of said second support means within said transparent tube.

10. A method for conducting an assay of a test substance comprising:
passing a test substance and an analytical reagent through the primary absorbent substance and then the analytical absorbent substance of the device of claim 1; and
detecting the last zone in said second fluid conducting means in which analytical reagent is absorbed.

11. The method of claim 10 wherein said test substance is an organic substance capable of being bound by a selected one of antibodies, antigens, binding proteins, bindable proteins, polysaccharides, antibiotics hormones and toxins.

12. The method of claim 11 wherein said test substance is a selected one of antibodies or antigens.

13. The method of claim 12 wherein said analytical reagent is selected from the group consisting of compounds having:
a first substance capable of being specifically bound by a selected one of said primary absorbent substance and said test substance;
a second substance capable of being specifically bound by said analytical absorbent substance; and
a detectable group.

14. The method of claim 13 wherein said second substance is selected from the group consisting of biotin, avidin, antigens, antibodies, enzymes, enzyme substrate analogues, and 2, 4-dinitrophenol.

15. The method of claim 14 wherein said second substance is a selected one of avidin and biotin.

16. The method of claim 13 wherein said detectable group is selected from the group consisting of colored dyes, enzymes, fluorescent compounds and radioisotopes.

17. The method of claim 16 wherein said detectable group is an enzyme.

18. A device for use in assaying a test substance comprising:
a funnel for catching and directing a downwardly flowing fluid to a small opening in said funnel;
a predetermined quantity of primary absorbent substance fixed within said funnel for contacting fluid flowing through said funnel and for selectively allowing only a quantity of an analytical reagent proportional to the quantity of test substance to pass through said funnel when a predetermined quantity of analytical reagent and said test substance are introduced into said funnel;
a narrow, transparent tube connected to receive downwardly flowing fluid from said small opening in said funnel;
a predetermined density of an analytical absorbent fixed within said tube for absorbing said analytical reagent such that when an analytical reagent is introduced into said tube said analytical reagent is sequentially absorbed within said tube and such that the length of said tube within which said analytical reagent is absorbed is proportional to the amount of said analytical reagent which is absorbed.

19. The device of claim 18 wherein said primary absorbent substance is selected from the group consisting of: antibodies, antigens, binding proteins, bindable substances, polysaccharides, antibiotics hormones and toxins.

20. The device of claim 18 wherein said analytical absorbent substance is selected from the group consisting of: avidin, biotin, antigens, antibodies, enzymes, enzyme substrate analogues and myeloma proteins.

21. The device of claim 20 wherein said analytical absorbent is a selected one of avidin and biotin.

22. A device for use in assaying a test substance comprising:
a fluid conducting means for receiving fluid and for conducting fluid therethrough;

selective passage means for interacting with said test substance such that only a quantity of an analytical reagent proportional to the quantity of said test substance can pass into said fluid conducting means when a predetermined quantity of analytical reagent and said test substance are introduced to said selective passage;

capture means for receiving and holding said analytical reagent; and a support means disposed in said fluid conducting means for holding a predetermined quantity of said capture means in each of a series of zones within said fluid conducting means such that a predetermined quantity of analytical reagent can be captured in each zone and such that as said analytical reagent passes through said fluid conducting means it is sequentially captured within said zones.

23. The device of claim 22 wherein said selective passage means comprises:

a predetermined quantity of a primary absorbent substance selected from the group consisting of antibodies, antigens, binding proteins, bindable proteins, polysaccharides, antibiotics, hormones and toxins disposed so that fluid entering said fluid conducting means can be contacted therewith;

wherein said capture means comprises a selected one of avidin and biotin; and wherein said support means comprises beads to which said capture means is bonded.

24. A device for use in assaying an analytical substance comprising:

capture means for receiving and holding said analytical substance;

a fluid conducting means having a series of zones through which fluid will sequentially pass as it passes through said fluid conducting means, each of said zones containing a predetermined quantity of said capture means for holding a predetermined quantity of said analytical substance such that as fluid containing said analytical substance passes through said fluid conducting means said analytical substance is sequentially captured within said zones; and means for detecting the last of said zones in which analytical substance is captured.

25. The device of claim 24 wherein said capture means comprises an analytical absorbent substance selected from the group consisting of avidin, biotin, antigens, antibodies, enzymes, enzyme substrate analogues and myeloma proteins.

26. The device of claim 25 wherein said fluid conducting means comprises a narrow, transparent tube and which further comprises a plurality of beads disposed within said tube to which said analytical absorbent is bonded.

27. The device of claim 26 wherein said analytical absorbent is a selected one of avidin and biotin.

28. A method for assaying a test substance comprising:

mixing a predetermined quantity of a primary absorbent substance with a predetermined quantity of an analytical substance and at least some test substance;

said primary absorbent substance being capable of binding said test substance and interacting with said test substance and said analytical substance so that upon said mixing step a portion of said analytical substance will be bound to said primary absorbent substance and a portion will not be bound, each of said portions being proportional to the quantity of said test substance mixed;

said analytical substance being capable of being specifically captured by the capture means of the device of claim 24;

separating the bound portion of said analytical substance from the unbound portion of said analytical substance;

introducing said unbound portion of said analytical substance into the capture means of the device of claim 24; and detecting the last of said zones of the device of claim 24 in which analytical substance is captured.

29. A method for assaying a test substance comprising:

mixing a predetermined quantity of a primary absorbent substance with a predetermined quantity of an analytical reagent and at least some test substance;

said primary absorbent substance being capable of binding said test substance and interacting with said test substance and said analytical reagent such that upon said mixing step a portion of said analytical reagent will be bound to said primary absorbent substance and a portion will not be bound; said analytical reagent being capable of being specifically bound by an analytical absorbent substance;

separating the bound portion of said analytical reagent from the unbound portion of said analytical reagent;

binding said unbound portion of said analytical reagent to an analytical absorbent substance; and detecting the presence of the analytical reagent bound to the analytical absorbent substance.

30. The method of claim 29 wherein said primary absorbent substance is selected from the group consisting of antibodies, antigens, binding proteins, bindable proteins, polysaccharides antibiotics hormones and toxins.

wherein said analytical absorbent substance is selected from the group consisting of avidin, biotin, antigens, antibodies, enzymes, enzyme substrate analogues and myeloma proteins; and wherein said analytical reagent is selected from the group consisting of compounds having a first substance capable of being bound by a selected one of said primary absorbent substance and said test substance, a second substance capable of being specifically bound by said analytical absorbent substance, and a detectable group.

31. The method of claim 30 wherein said second substance is selected from the group consisting of biotin, avidin, antigens, antibodies, enzymes, enzyme substrate analogues, and 2, 4-dinitrophenol.

32. The method of claim 31 wherein said second substance is a selected one of avidin and biotin.

33. The method of claim 31 wherein said detectable group is selected from the group consisting of colored dyes, enzymes, fluorescent compounds and radioisotopes.

34. The method of claim 33 wherein said detectable group is an enzyme.

35. A method for assaying a test substance comprising:

fixing a predetermined quantity of a primary absorbent substance in a first fluid-conducting zone, said primary absorbent substance being capable of interacting with said test substance and an analytical reagent such that a portion of said analytical reagent will be bound within said first zone and a portion will not be bound within said first zone as said analytical reagent and said test substance are conducted through said first zone, each of said portions being proportional to the quantity of said test substance introduced into said first zone;

introducing a predetermined quantity of said analytical reagent and said test substance into said first zone;

preparing a series of fluid-conducting zones each of which has fixed therein an analytical absorbent capable of specifically binding said analytical reagent;

sequentially introducing the unbound portion of said analytical reagent from said first zone into said series of zones until all of said analytical reagent has been bound; and detecting the last zone of said series of zones in which said analytical reagent is bound.

36. The method of claim 35 wherein:

said primary absorbent substance is selected from the group consisting of antibodies, antigens, binding proteins, bindable proteins, polysaccharides, antibiotics and toxins;

wherein said analytical absorbent substance is selected from the group consisting of avidin, biotin, antigens, antibodies, enzymes, enzyme substrate analogues and myeloma proteins; and wherein said analytical reagent is selected from the group consisting of compounds having a first substance capable of being bound by a selected one of said primary absorbent substance and said test substance, a second substance capable of being specifically bound by said analytical absorbent substance and a detectable group.

37. The method of claim 36 wherein said second substance is selected from the group consisting of biotin, avidin, antigens, antibodies, enzymes, enzyme substrate analogues, and 2, 4-dinitrophenol.

38. The method of claim 37 wherein said second substance is a selected one of avidin and biotin.

39. The method of claim 37 wherein said detectable group is selected from the group consisting of colored dyes, enzymes, fluorescent compounds and radioisotopes.

40. The method of claim 39 wherein said detectable group is an enzyme.

* * * * *